United States Patent
Fisher et al.

(10) Patent No.: US 8,486,115 B2
(45) Date of Patent: Jul. 16, 2013

(54) SPINAL PLATE ASSEMBLIES WITH BACKOUT PROTECTION CAP AND METHODS

(75) Inventors: James Fisher, Broomfield, CO (US); Alan Burkholder, Denver, CO (US); Michael Fulton, Superior, CO (US)

(73) Assignee: Lanx, Inc., Broomfield, CO (US)

( * ) Notice: Subject to any disclaimer, the term of this patent is extended or adjusted under 35 U.S.C. 154(b) by 832 days.

(21) Appl. No.: 12/404,051

(22) Filed: Mar. 13, 2009

(65) Prior Publication Data
US 2010/0234897 A1    Sep. 16, 2010

(51) Int. Cl.
*A61B 17/80*    (2006.01)
(52) U.S. Cl.
USPC ........................................... 606/286; 606/295
(58) Field of Classification Search
USPC ................. 606/286, 293, 295, 296, 298, 300, 606/301; 411/372.1, 373
See application file for complete search history.

(56) References Cited

U.S. PATENT DOCUMENTS

| | | |
|---|---|---|
| 2,409,638 A | 10/1946 | Lyon |
| 3,486,505 A | 12/1969 | Morrison |
| 3,711,347 A | 1/1973 | Wagner et al. |
| 3,750,652 A | 8/1973 | Sherwin |
| 3,834,021 A | 9/1974 | White et al. |
| 4,794,918 A | 1/1989 | Wolter |
| 5,085,660 A | 2/1992 | Lin |
| 5,364,399 A | 11/1994 | Lowery et al. |
| 5,407,312 A | 4/1995 | Terrizzi |
| 5,558,674 A | 9/1996 | Heggeness et al. |
| 5,578,034 A | 11/1996 | Estes |
| 5,676,666 A | 10/1997 | Oxland et al. |
| 5,741,258 A | 4/1998 | Klaue et al. |
| 5,782,830 A | 7/1998 | Farris |
| 5,885,299 A | 3/1999 | Winslow et al. |
| 5,904,683 A | 5/1999 | Pohndorf et al. |
| 5,951,558 A | 9/1999 | Fiz |
| 5,954,722 A | 9/1999 | Bono |
| 5,957,927 A | 9/1999 | Magee et al. |
| 6,129,730 A | 10/2000 | Bono et al. |
| 6,139,550 A | 10/2000 | Michelson |
| 6,152,927 A | 11/2000 | Farris et al. |
| 6,159,213 A | 12/2000 | Rogozinski |
| 6,193,721 B1 | 2/2001 | Michelson |
| 6,224,599 B1 | 5/2001 | Baynham et al. |
| 6,224,602 B1 | 5/2001 | Hayes |
| 6,235,033 B1 | 5/2001 | Brace et al. |
| 6,235,034 B1 | 5/2001 | Bray |
| 6,258,089 B1 | 7/2001 | Campbell et al. |
| 6,261,291 B1 | 7/2001 | Talaber et al. |

(Continued)

FOREIGN PATENT DOCUMENTS
WO    WO 99/56653    11/1999

*Primary Examiner* — Ralph Lewis
(74) *Attorney, Agent, or Firm* — Perkins Coie LLP

(57) ABSTRACT

A bone plate assembly includes a plate, at least one bone screw, and at least one cap member. The screw extends into a through hole of the plate and a head of the screw seats in the through hole. The plate includes an undercut slot adjacent to the through hole. The cap includes at least one tab member that extends radially outward. The cap is mounted in the through hole with the tab member positioned in the undercut slot to inhibit the screw from backing out of the plate. In some arrangements, the tab member is rotatable within the undercut slot from an unlocked position to a locked position.

15 Claims, 11 Drawing Sheets

U.S. PATENT DOCUMENTS

| | | |
|---|---|---|
| 6,261,296 B1 | 7/2001 | Aebi et al. |
| 6,306,139 B1 | 10/2001 | Fuentes |
| 6,413,259 B1 | 7/2002 | Lyons et al. |
| 6,436,101 B1 | 8/2002 | Hamada |
| 6,503,250 B2 | 1/2003 | Paul |
| 6,533,786 B1 | 3/2003 | Needham et al. |
| 6,565,303 B1 | 5/2003 | Riccitellie et al. |
| 6,626,907 B2 | 9/2003 | Campbell et al. |
| 6,695,846 B2 | 2/2004 | Richelsoph et al. |
| 7,094,239 B1 * | 8/2006 | Michelson ............ 606/70 |
| 7,172,593 B2 | 2/2007 | Trieu et al. |
| 7,229,443 B2 | 6/2007 | Eberlein et al. |
| 2001/0001119 A1 | 5/2001 | Lombardo |
| 2001/0041894 A1 | 11/2001 | Campbell et al. |
| 2001/0047174 A1 * | 11/2001 | Donno et al. ............ 606/73 |
| 2002/0015189 A1 | 2/2002 | Miyajima |
| 2002/0120273 A1 | 8/2002 | Needham et al. |
| 2003/0040749 A1 | 2/2003 | Grabowski et al. |
| 2003/0060828 A1 | 3/2003 | Michelson |
| 2003/0078583 A1 | 4/2003 | Biedermann et al. |
| 2006/0149241 A1 * | 7/2006 | Richelsoph et al. ............ 606/61 |
| 2007/0239163 A1 * | 10/2007 | Strnad et al. ............ 606/72 |
| 2009/0149887 A1 * | 6/2009 | Schlaepfer et al. ............ 606/278 |
| 2011/0160776 A1 * | 6/2011 | Erickson et al. ............ 606/286 |

* cited by examiner

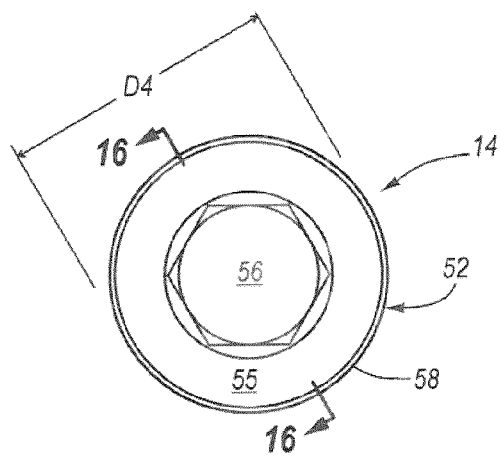
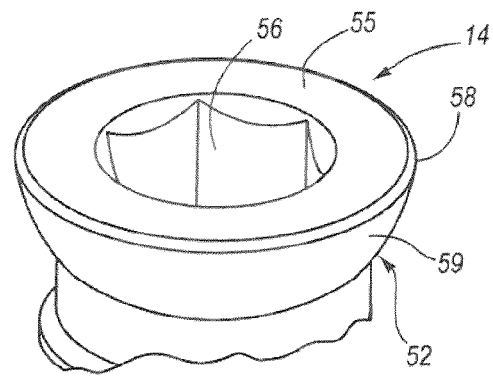
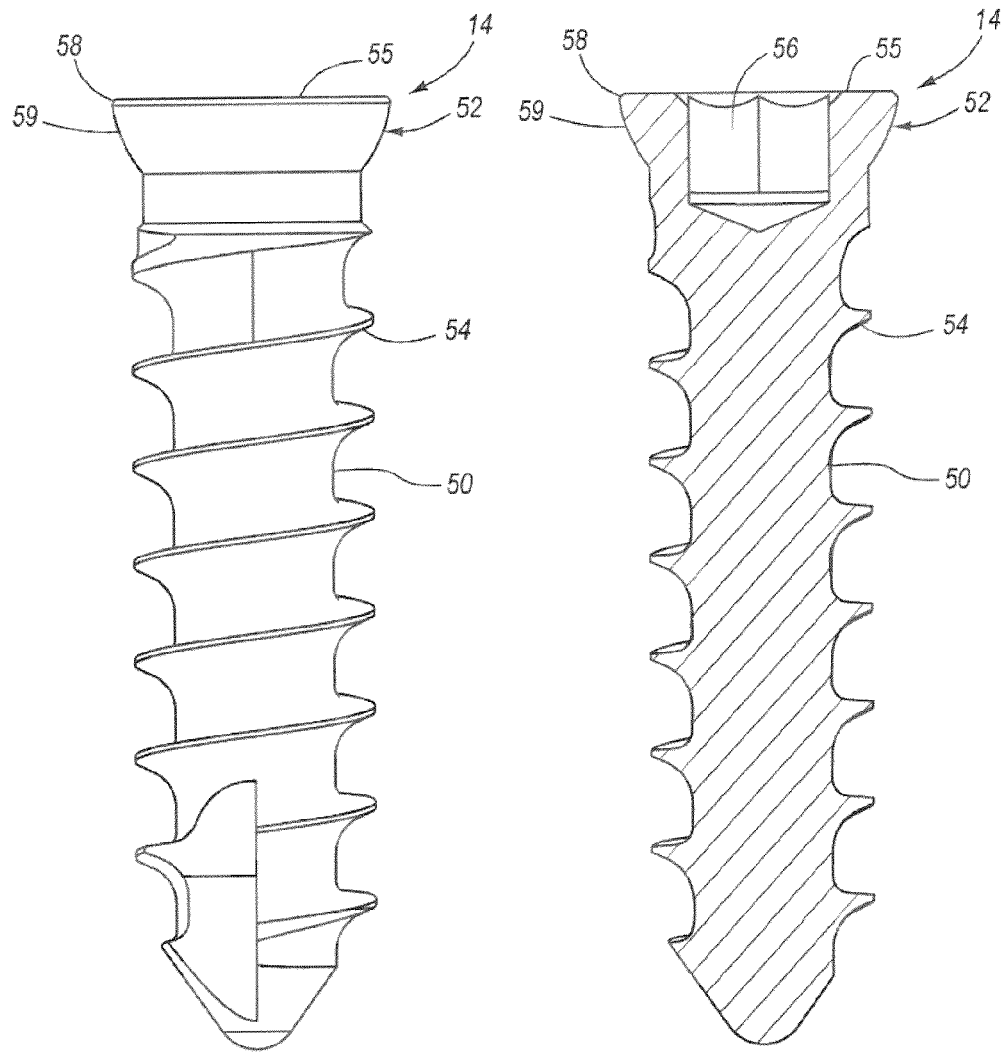
FIG. 15
FIG. 17
FIG. 14
FIG. 16

SPINAL PLATE ASSEMBLIES WITH BACKOUT PROTECTION CAP AND METHODS

FIELD OF THE INVENTION

The present disclosure generally relates to spinal implants and associated methods, and more particularly relates to cervical plate assemblies having a backout protection cap.

BACKGROUND

The vertebrae of the human spine are arranged in a column with one vertebra on top of the next. An intervertebral disc lies between adjacent vertebrae to transmit force between the adjacent vertebrae and provide a cushion between them. The discs allow the spine to flex and twist. With age, spinal discs begin to break down, or degenerate, resulting in the loss of fluid in the discs and consequently resulting in them becoming less flexible. Likewise, the disks become thinner allowing the vertebrae to move closer together. Degeneration may also result in tears or cracks in the outer layer, or annulus, of the disc. The disc may begin to bulge outwardly. In more severe cases, the inner material of the disc, or nucleus, may actually extrude out of the disc. In addition to degenerative changes in the disc, the spine may undergo changes due to trauma from automobile accidents, falls, heavy lifting, and other activities. Furthermore, in a process known as spinal stenosis, the spinal canal narrows due to excessive bone growth, thickening of tissue in the canal (such as ligament), or both. In all of these conditions, the spaces through which the spinal cord and the spinal nerve roots pass may become narrowed, leading to pressure on the nerve tissue which can cause pain, numbness, weakness, or even paralysis in various parts of the body. Finally, the facet joints between adjacent vertebrae may degenerate and cause localized and/or radiating pain. All of the above conditions are collectively referred to herein as spine disease.

Conventionally, surgeons treat spine disease by attempting to restore the normal spacing between adjacent vertebrae. This may be sufficient to relieve pressure from affected nerve tissue. However, it is often necessary to also surgically remove disc material, bone, or other tissues that impinge on the nerve tissue and/or to debride the facet joints. Most often, the restoration of vertebral spacing is accomplished by inserting a rigid spacer made of bone, metal, or plastic into the disc space between the adjacent vertebrae and allowing the vertebrae to grow together, or fuse, into a single piece of bone. The vertebrae are typically stabilized during this fusion process with the use of bone plates and/or pedicle screws fastened to the adjacent vertebrae.

Typically a plurality of bone screws are used to secure a plate to the vertebrae. The bone screws, absent a screw retention mechanism, may backout. Screw retention mechanisms have been developed to inhibit the bone screws from backing out. Some of the devices include caps or plates that extend over the screw holes in the plate to inhibit upward movement of bone screws relative to the plate. Other devices include a frictional engagement between a bushing and the bone screws.

Although some devices exist for inhibiting backing out of bone screws, further advances in this area are possible.

SUMMARY

One aspect of the present disclosure relates to a cervical plate assembly that includes a plate, at least one bone screw, and at least one cap member. The screw extends into a through hole of the plate and a head of the screw seats in the through hole. The plate includes an undercut slot adjacent to the through hole. The cap includes at least one tab member that extends radially outwardly. The cap is mounted in the through hole with the tab member positioned in the undercut slot to inhibit the screw from backing out of the plate. In some arrangements, the tab member is rotatable within the undercut slot from an unlocked position to a locked position.

The foregoing and other features, utilities and advantages of the invention will be apparent from the following more particular description of a preferred embodiment of the invention as illustrated in the accompanying drawings.

BRIEF DESCRIPTION OF THE DRAWINGS

The accompanying drawings, which are incorporated in and constitute a part of this specification, illustrate embodiments of the present invention, and together with the description, serve to explain the principles thereof. Like items in the drawings are referred to using the same numerical reference.

FIG. 14 is a side view of the screw of the spine plate assembly of FIG. 1;

FIG. 15 is a top view of the screw of the spine plate assembly of FIG. 1;

FIG. 16 is a cross-sectional view of the screw of the spine plate assembly of FIG. 1;

FIG. 17 is a close-up view of a head portion of the screw of FIG. 11;

DETAILED DESCRIPTION

Figure 1:
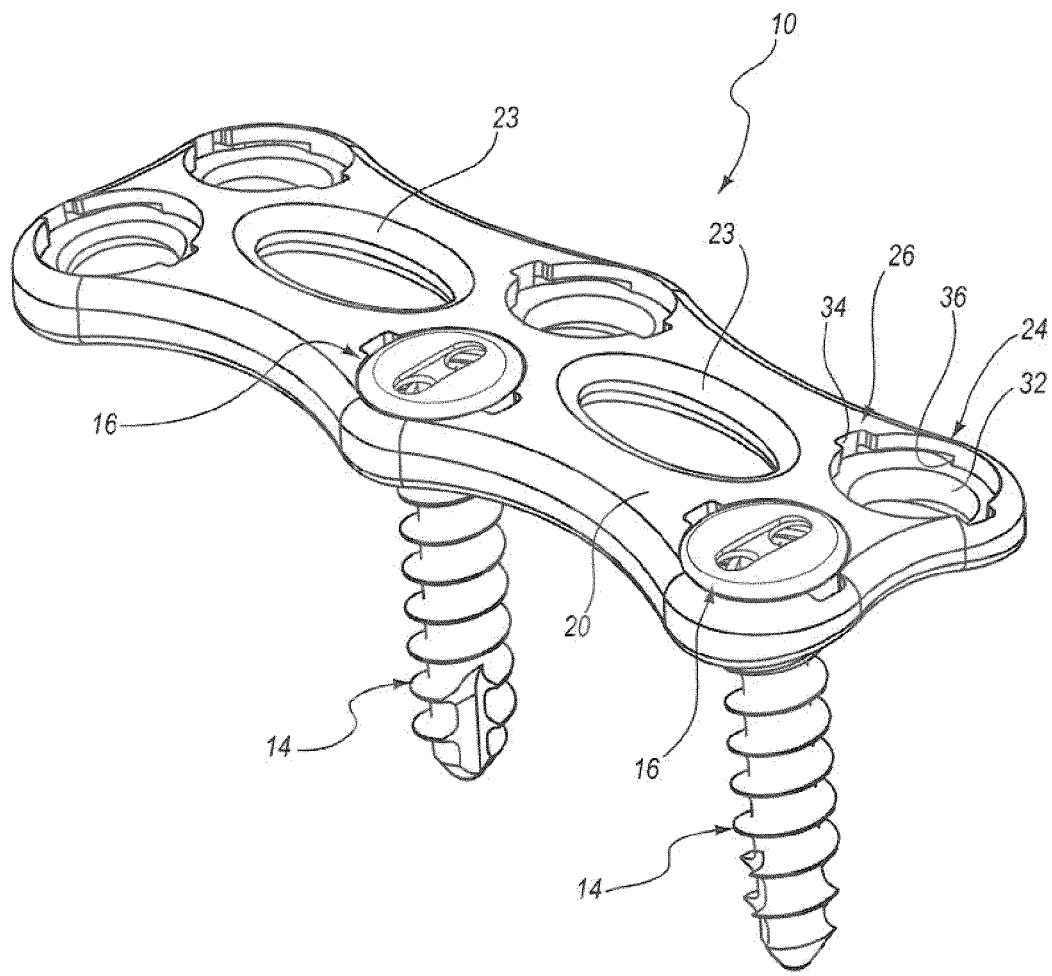
FIG. 1 is a perspective view of a spine plate assembly according to the present disclosure.

The present disclosure is directed to a bone plate assembly that includes a cap member that helps retain a screw relative to a bone plate. Typically, the screw is inserted into a through hole of the plate until the head of the screw is lodged in a seat surface defined in the through hole. The cap member is then inserted into the through hole and secured to the plate to prevent backing out of the screw relative to the plate.

In the past, cap members, having a plurality of externally positioned threads, have been threadably mounted into the through hole after insertion of the screw to prevent backing out of the screw relative to the plate. Typically, such threaded cap members have not performed well because there is limited space on the cap member and plate for mounting sufficient thread structure.

In one example, the present disclosure is directed to a cap member that mounts within a recess in a bone plate and is rotatable about an axis between a locked and an unlocked position. The cap member and recess are sized and shaped to provide increasing torsional resistance over at least a portion of the rotational movement in response to rotation of the cap member from the unlocked position to the locked position. In another example, the assembly is responsive to continued rotation toward the locked position to reach a maximum torsional resistance after which continued rotation results in a decrease in torsional resistance. In another example, rotation of the cap from the locked position to the unlocked position results in increasing torsional resistance over at least a portion of the rotational movement. The change in torsional resistance may be produced by non-circular shaped caps and/or recesses, protrusions, tabs, off-center rotation, and/or other mechanisms. For example, a non-circular cap may abut the side of the recess with increasing interference in response to rotation. Similarly, a circular cap may be mounted in such a way as to rotate about an axis off-set from its geometric center. Similarly, a cap may have a tab extending outwardly that engages a feature in the recess.

In another example, a cap member includes at least one tab member that extends radially outwardly from a peripheral surface of the cap member. The tab member inserts into an undercut slot structure defined in the plate. Typically, the tab member has sufficient structure (i.e., width, thickness and length) for locking of the cap member in a fixed position relative to the plate. Fixed position in the context of the present application does not mean fixed and unmovable as the cap member may move relative to the plate once locked depending on tolerances and the like. The undercut slot usually includes an access opening along a top or anterior surface of the plate so that the tab member can enter into the undercut slot as the cap member is placed in the through hole. Rotation of the cap member moves the tab from an unlocked position to a locked position within the undercut slot. In some arrangements, a plurality of tab members may be positioned around a periphery of the cap member to provide additional engagement between the cap member and the plate. The varying torsional resistance feature may be combined and the tabbed cap.

Figure 5:
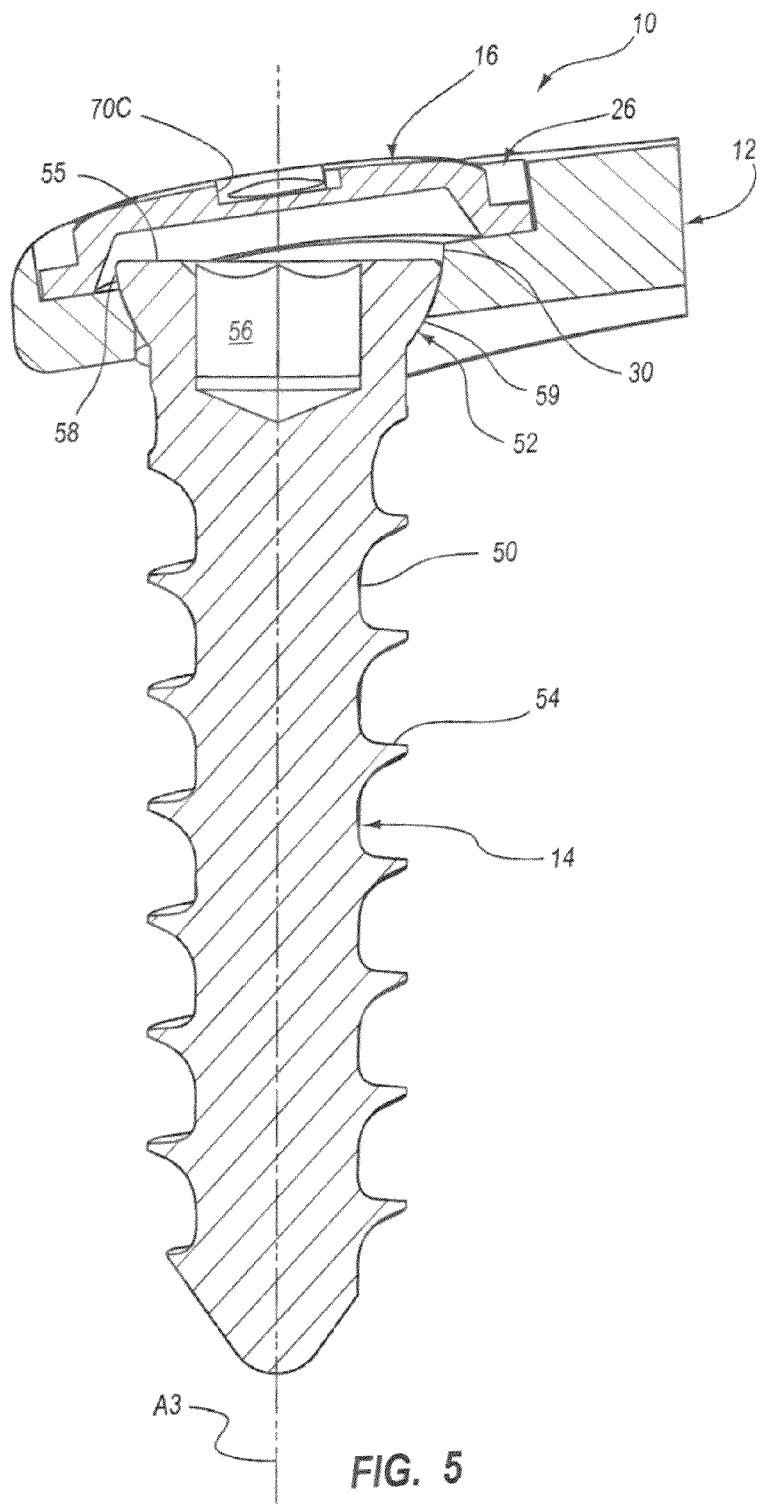
FIG. 5 is a cross-sectional view of the spine plate assembly of FIG. 1 with the cap in a first rotated position.
Figure 6:
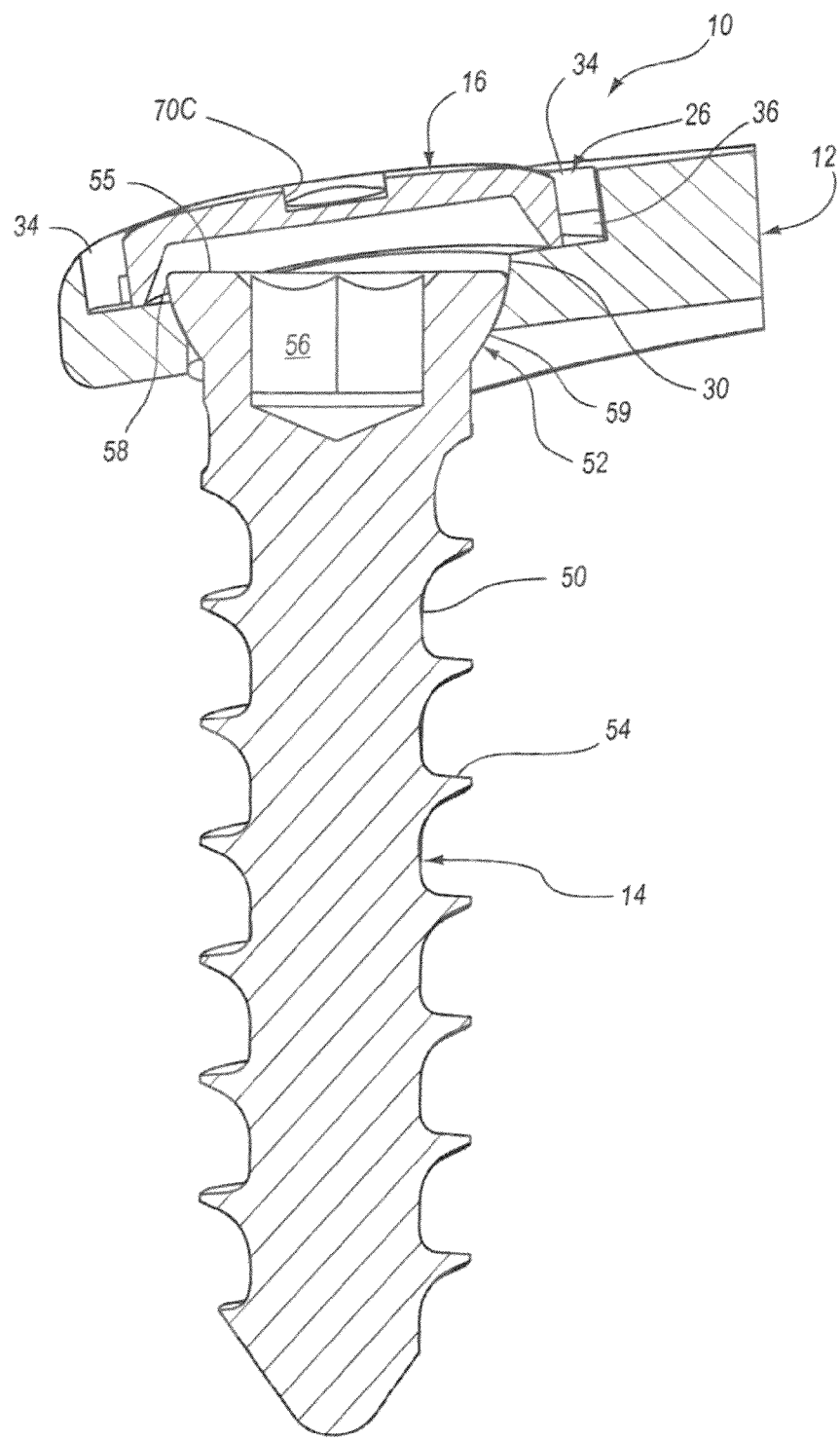
FIG. 6 is a cross-sectional view of the spine plate assembly of FIG. 1 with the cap in a second rotated position.

Referring now to FIGS. 1-19, an example bone plate assembly 10 is shown and described. Bone plate assembly 10 includes a plate 12, at least one screw 14, and at least one cap member 16. Referring first to FIG. 2, the plate 12 includes a plurality of through holes 24 into which one of the plurality of screws 14 is inserted. The screws 14 are inserted a sufficient distance until a head of the screw 14 engages a seat portion of the through hole 24. One of the cap members 16 is then positioned in the through hole 24 and rotated from an unlocked position shown in FIGS. 3 and 5 to a locked position shown in FIGS. 1, 3 and 6.

The plate 12 includes a top surface 20, a bottom surface 22, a plurality of through holes 24, and a locking recess 26 associated with each of the through holes 24. The top surface 20 is sometimes referred to as an anterior surface of the plate 12. The bottom surface 22 is sometimes referred to as a posterior surface of the plate 12.

Figure 2:
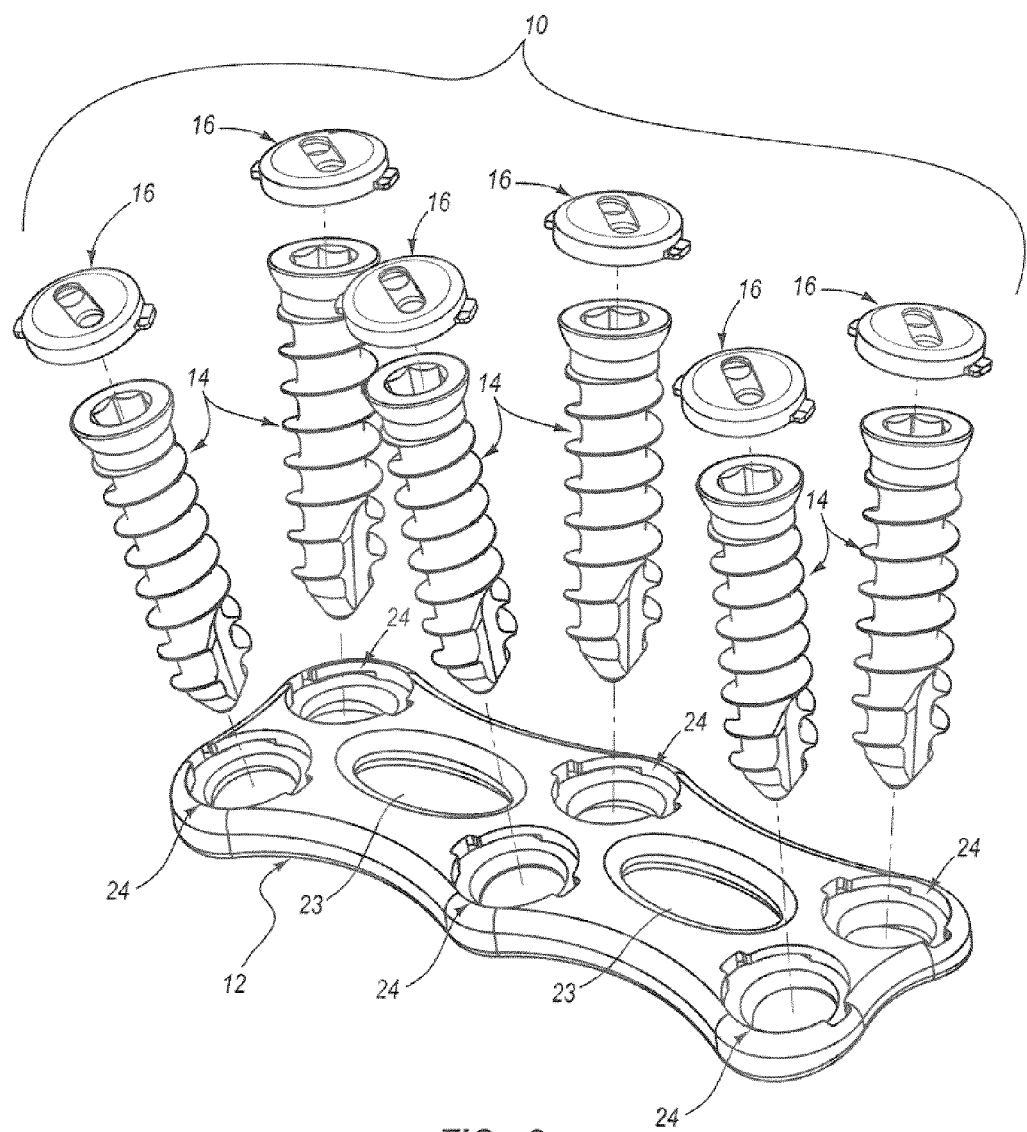
FIG. 2 is an exploded perspective view of the spine plate assembly of FIG. 1 including additional screw and cap members.
Figure 18:
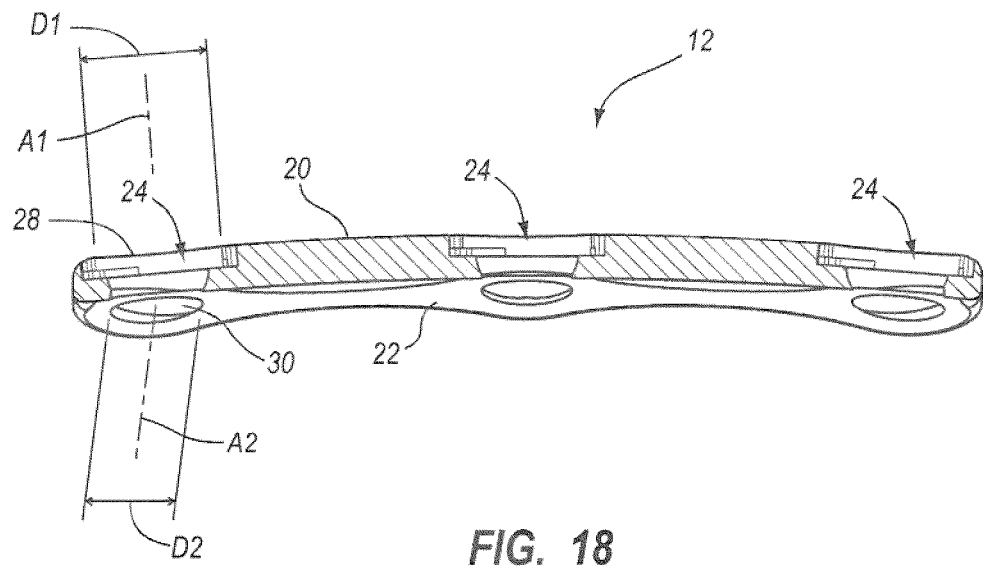
FIG. 18 is a first cross-sectional view of the plate of the spine plate assembly of FIG. 1.
Figure 19:
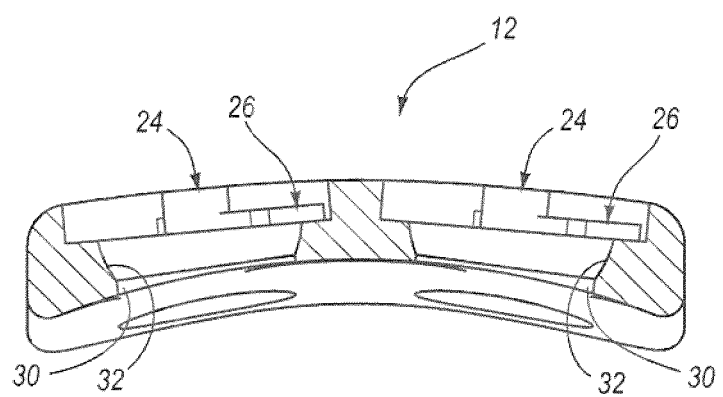
FIG. 19 is a second cross-sectional view of the plate of the spine plate assembly of FIG. 1.
Figure 20A:
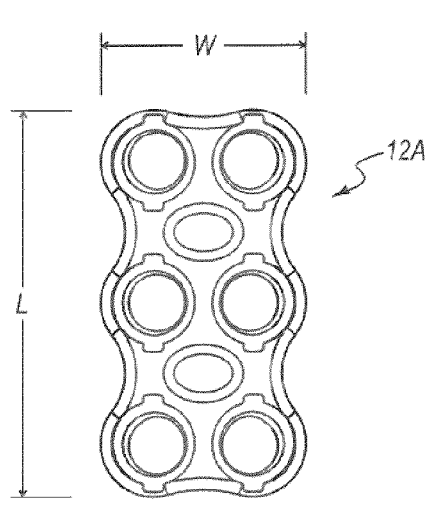
FIGS. 20A-D are top views of several alternative plate embodiments for use with the spine plate assembly of FIG. 1.
Figure 20B:
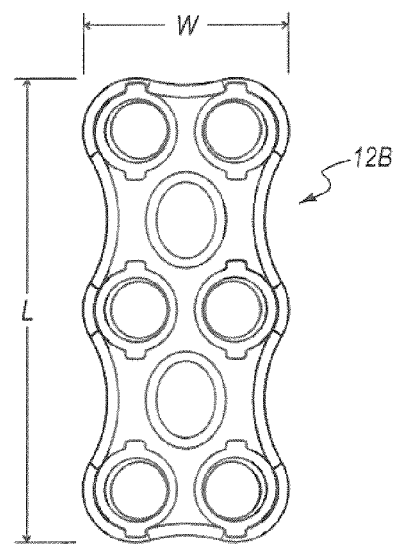
Figure 20C:
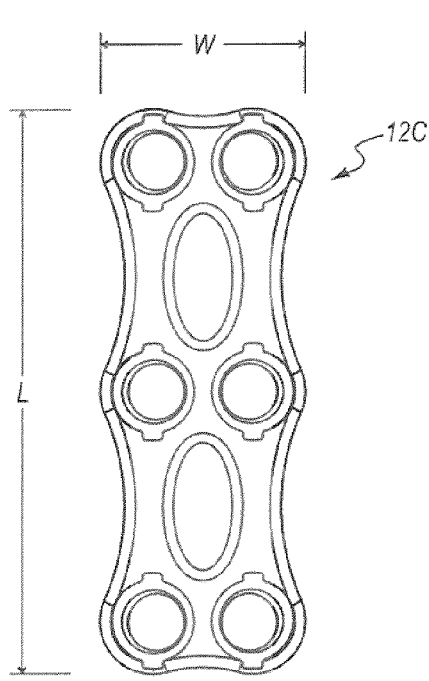
Figure 20D:
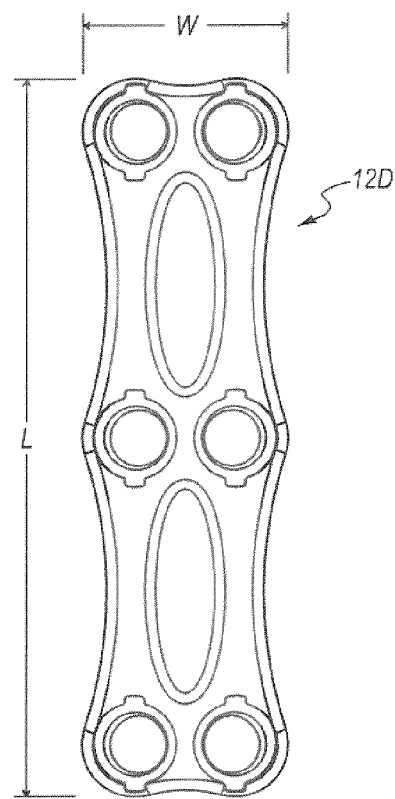

Referring to FIGS. 1, 18 and 19, each of the through holes 24 includes an entrance portion 28 positioned adjacent to the top surface 20, and an exit portion 30 positioned adjacent to the bottom surface 22. A head seat surface 32 is defined in the through holes 24 at a location between the entrance portion 28 and the exit portion 30. The entrance portion 28 has an entrance diameter D1 and is arranged along an axis A1. The exit portion 30 has an exit diameter D2 and is arranged along an axis A2. The axis A1 may be arranged coaxial with the axis A2. Alternatively, as shown in at least FIG. 18, the axis A1 may be arranged at an angle (i.e., non-coaxially and/or non-parallel) with the axis A2.

The locking recess 26 is shown in further detail with reference to at least FIGS. 1, 7, 18 and 19. The locking recess 26 includes a top opening 34 accessible along the top surface 20, and a side opening 36 accessible from within the entrance portion 28 of the through hole 24. The top opening 34 is sized to permit entrance of a tab member of the cap member 16 as the cap member is inserted into one of the through holes 24 as will be described in further detail below. The side opening 36 permits rotation of the cap member 16 while the cap member 16 is positioned within the through hole 24 and the tab member of the cap member 16 is residing in the locking recess 26.

Figure 7:
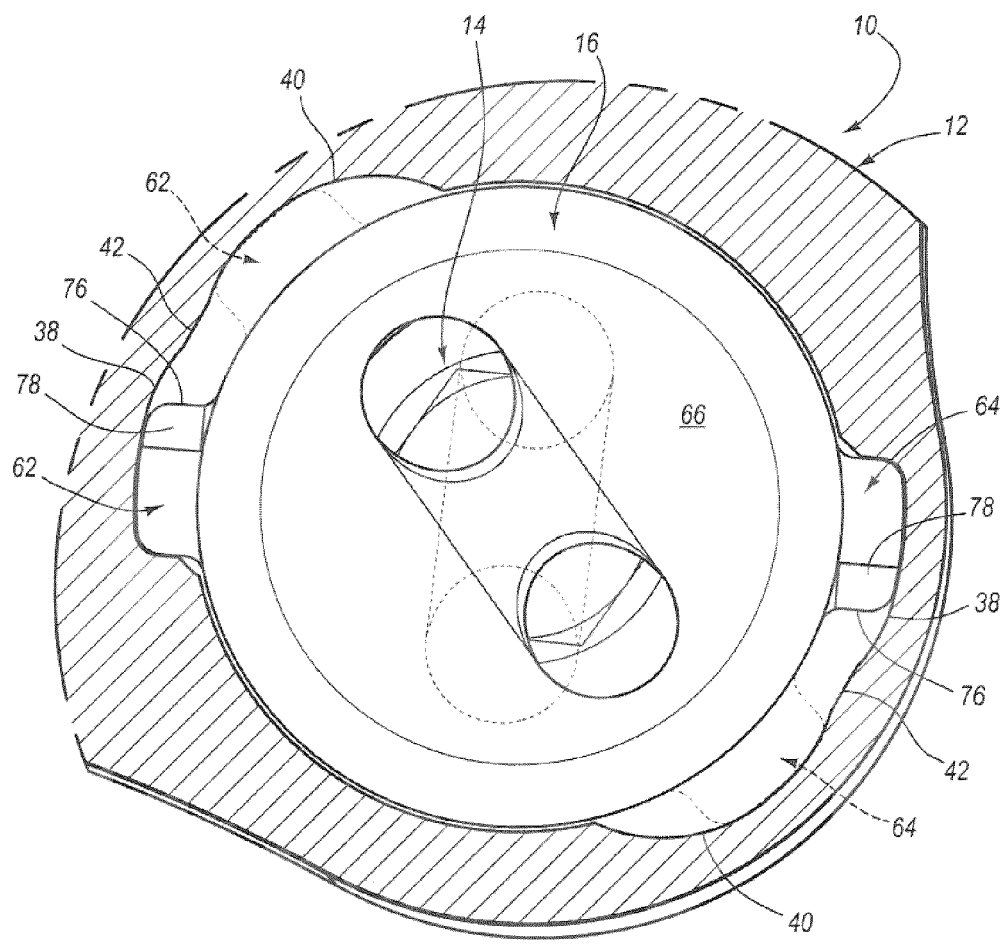
FIG. 7 is a top view of the spine plate assembly of FIG. 1 with the plate partially cut away to show features of a locking recess of the plate.

The locking recess includes first and second portions 38, 40 as shown in FIG. 7. The first and second portions 38, 40 are each sized to receive the tab member of the cap member 16. The first and second portions 38, 40 are separated by a locking protrusion 42 that partially protrudes into a pathway through which the tab member of the cap member 16 must pass as the cap member 16 rotates between unlocked and locked positions. FIG. 7 illustrates a tab member 62 of the cap member 16 in solid lines positioned within the first portion 38. FIG. 7 also illustrates the tab member 62 in broken lines within the second portion 42 after the cap member 16 has been rotated in a clockwise direction from the unlocked to the locked position. The protrusion 42 may take any number of shapes including polygonal shapes, elliptical shapes, or random shapes.

The locking protrusion 42 is adapted and configured to limit counter-clockwise rotation of the cap member 16 after the tab member of the cap member 16 resides in the second portion 40 of the locking recess 26. The locking protrusion 42 also provides a "positive lock" type feature for the operator. When the operator is rotating a cap member 16 in the clockwise direction, the operator can feel an increase in resistance to clockwise rotation as the tab member moves past the locking protrusion 42, and then a reduction in resistance to rotation in a clockwise direction as the tab member moves past the locking protrusion 42. Sometimes, the operator can feel or hear a "clicking" or "latching" effect as the tab member moves past the locking protrusion from a location in the first portion 38 to a location in the second portion 40. The tab may engage the locking recess, e.g., the side opening 36 to create some resistance to rotation at all positions with increased resistance as the tab moves past the lock protrusion. Alternatively, the tab sized recess may be spaced from the side opening in one or both of the first and second portions 38, 40. Alternatively, the tab and recess may be sized to provide an increasing interference fit to lock the cap and the protrusion 42 may be omitted.

Typically, the cap member 16 cannot be rotated in a counter-clockwise direction to move the tab member from the second portion 40 of the locking recess 26 (i.e., the locked position) past the locking-protrusion 42 to a location in the first portion 38 of the locking recess 26 (i.e., the unlocked position) without application of a substantial rotational force in the counter-clockwise direction. Such a force applied in the counter-clockwise direction cannot be applied by the screw 14 or cap member 16 alone, but typically can be applied by an operator who intentionally applies that force to the cap member 16 with an instrument.

The cap member 16 is generally described as being rotated or moved to the locked position by rotating or moving the cap member 16 in the clockwise direction and rotated or moved to the unlocked position by rotating or moving the cap member 16 in the counter-clockwise direction. It should be appreciated, however, that the direction of rotation or movement to lock or unlock cap member 16 is a matter of design choice.

Figure 3:
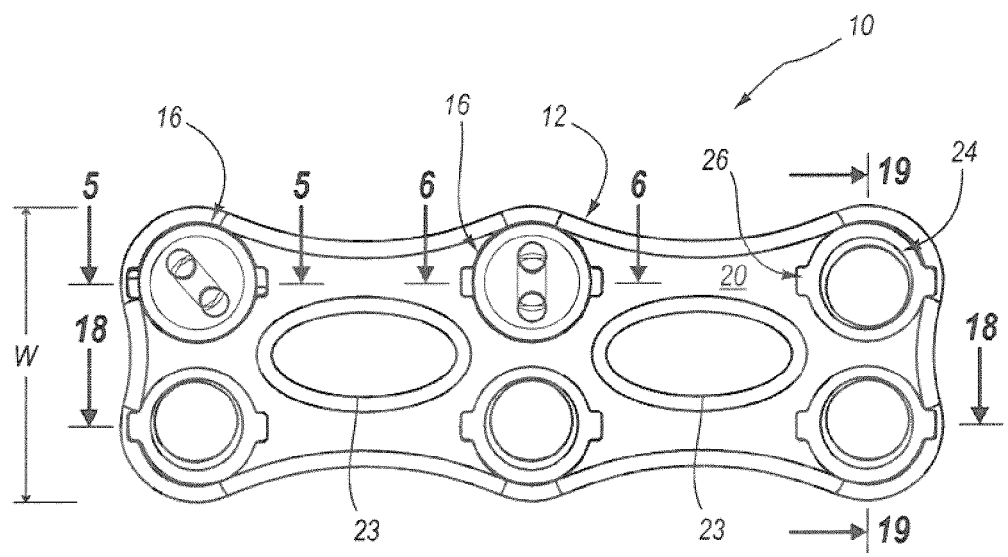
FIG. 3 is a top view of the spine plate assembly of FIG. 1.
Figure 4:
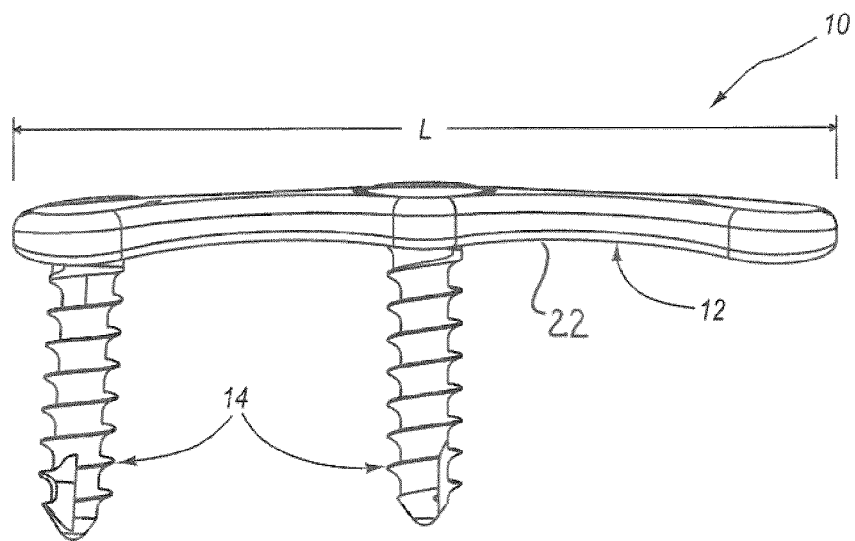
FIG. 4 is a side view of the spine plate assembly of FIG. 1.

The plate 12 may include a length L and a width W as shown in FIGS. 3 and 4. Furthermore, the plate 12 may have at least one viewing window 23 to provide viewing of the intervertebral space. The plate 12 has a construction that may span multiple intervertebral spaces, such as a pair of intervertebral spaces (also known as a two-level cervical plate). However, the plate 12 may be constructed to pan more or fewer intervertebral spaces. Other numbers, shapes and sizes of windows 23 may be included in other embodiments.

FIGS. 20A-D illustrate some additional plate constructions having different lengths L for a given width W. The plates 12A-12D shown in FIGS. 20A-20D are merely exemplary of the many different plate constructions that are possible. Similarly, the width W may vary among plates of a given length L. In other arrangements, both the width W and the length L may vary among different plates. Furthermore, the plates shown in FIGS. 20A-20D are all depicted as 2-level plates. Similar size variation may be made with 1-level plates, 3-level plates, 4-level plates or plates for any number of levels. Many different plate constructions are possible for applications on different intervertebral spaces.

The screw 14 includes a shank 50 and a head 52 as shown with reference to at least FIGS. 14-17. The head 52 defines a top surface 55, a top perimeter edge 58, and a seat surface 59. A plurality of threads 54 are included along the shank 50. An instrument recess 56 is defined in the top surface 55 and is adapted and configured for receiving a portion of an insertion instrument that may apply a rotational, torque force to the screw for insertion of the screw into bone material of a patient. The seat surface 59 is configured for engagement with the seat surface 32 of the through holes 24 in the plate 12. The generally contoured or curved shape of the seat surface 59, when mated with the generally contoured or curved surface of the seat surface 32, may provide some rotation of the screw 14 relative to the plate 12. For example, the screw 14 may move from side-to-side to varying orientation of a longitudinal axis A3 of the screw 14 (see FIG. 5) relative to an axis A2 of the exit portion 30 of the through hole 24 (see FIG. 18). This side-to-side rotational movement of the screw 14 relative to the plate 12 may alter a position of the top perimeter edge 58 of the screw relative to the cap 16. A bottom or underside of the cap 16 may be configured (as described below) to accommodate various positions of the perimeter edge 58 when the screw 14 is seated against the seat surface 32 in through hole 24.

Figure 8:
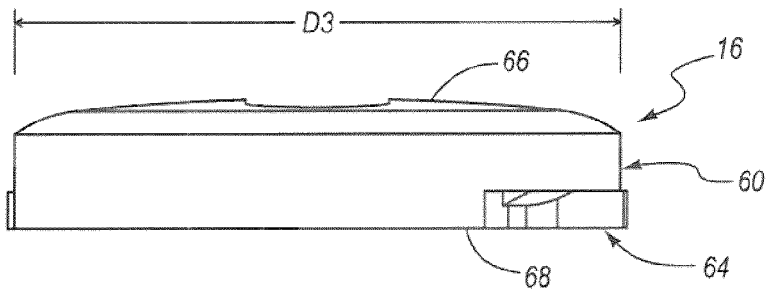
FIG. 8 is a side view of the cap of the spine plate assembly of FIG. 1.
Figure 9:
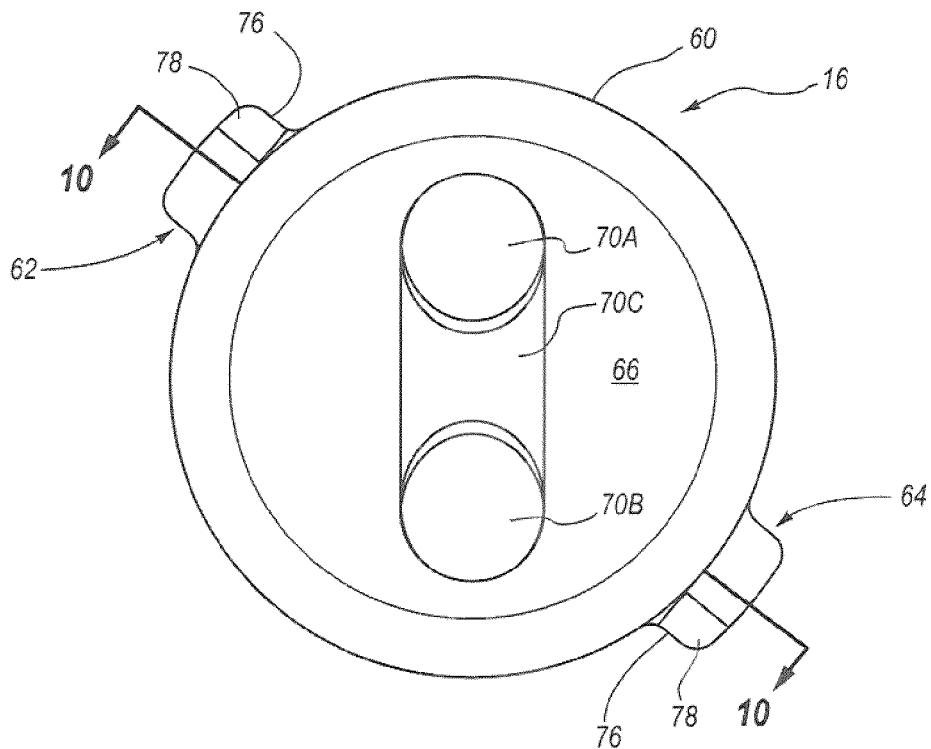
FIG. 9 is a top view of the cap of the spine plate assembly of FIG. 1.

The cap member 16 includes a body portion 60 and first and second tab members 62, 64 as shown and described with reference to FIGS. 8-10. The body portion 60 includes a top surface 66, a bottom surface 68, a plurality of instrument recesses 70A-C defined in the top surface 66, and a screw recess 72 position along the bottom surface 68. The body portion 60 may have a maximum diameter or dimension D3. Typically, the dimension D3 is smaller than the dimension D1 of the entrance portion 28 of the through hole 24.

Figure 11:
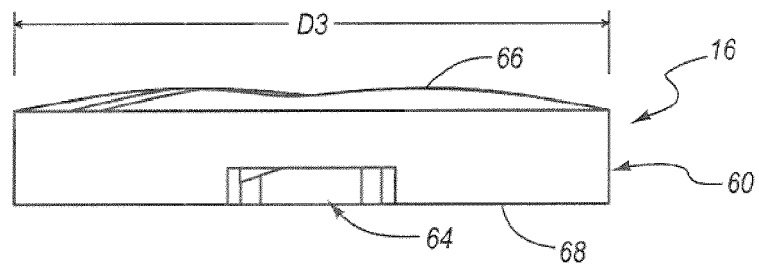
FIG. 11 is a side view of another cap embodiment for use with the spine plate assembly of FIG. 1.
Figure 12:
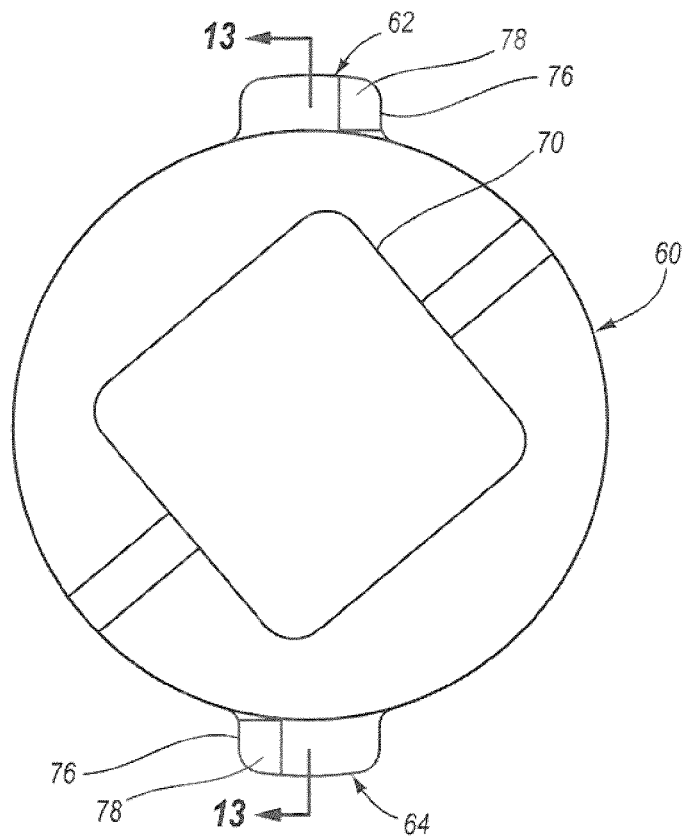
FIG. 12 is a top view of the cap of FIG. 10.
Figure 13:
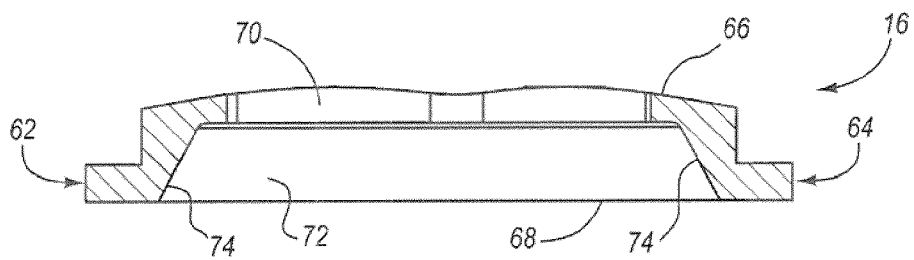
FIG. 13 is a cross-sectional view of the cap of FIG. 10.

The instrument recesses 70A-B are constructed as through holes having a generally circular cross-section. The recess 70C has a generally oval cross-section and has a depth that extends only partially through the thickness of the body portion 60. The recesses 70A-C are configured for engagement by an insertion instrument having a particular construction. Other instrument recess configurations are possible, such as the instrument recess 70 shown with reference to the cap member embodiment of FIGS. 11-13. The instrument recess 70 may have a generally square cross-section and passes through an entire thickness of the body portion 60 in FIGS. 11-13. A cap member 16 as shown in FIGS. 11-13 with an instrument recess 70 larger than the instrument recess 56 in the screw 14 permits the screw to be turned after the cap member 16 is mounted to the plate by passing a screw driver through the instrument recess 70 to engage the instrument recess 56.

Figure 10:
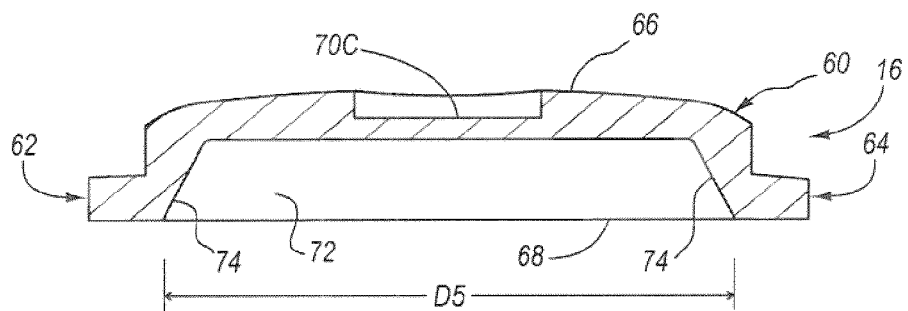
FIG. 10 is a cross-sectional view of the cap of the spine plate assembly of FIG. 1.

The screw recess 72 has a maximum diameter or dimension D5 (see FIG. 10). The dimension D5 is typically greater than the dimension D4 of the head 52 of the screw 14 (FIG. 15). The screw recess 72 may include a tapered surface 74.

The tab members 62, 64 each include a leading edge 76 facing in a direction of rotation of the cap member 16 from the unlocked position to the locked position (i.e., in the clockwise direction with the examples shown in the attached figures). The tab members 62, 64 may include a tapered portion 78 extending from the leading edge 76. The tapered portion 78 may provide easier insertion of the tab members 62, 64 into the locking recess 26, in particular when rotating the tab member 62, 64 from the unlocked position to the locked position.

In some arrangements, only a single tab member may be necessary for connecting the cap member 16 to the plate 12. In other arrangements, more than two tab members may be used. The shape and size of the tab members 62, 64 may vary from the construction shown in the attached figures. Further, the shape and size of the locking recess 26 and the plate 12 may vary as needed to accommodate different shapes and sizes as well as numbers of tab members for a given cap member 16.

The cap member of the present disclosure may be generally described as a locking cap that is operable to obtain a locked orientation relative to the plate by rotation within a locking recess defined in the plate. The locking recess may be an undercut feature that is defined in the plate spaced between the top and bottom surfaces of the plate. The locking recess may have access via the top surface of the plate and from within a through hole defined in the plate. The locking recess may include a protrusion, latch or other feature that provides resistance to rotational movement of the cap after the cap has been moved into a locked position relative to the plate.

In some arrangements, the cap member may be operable to move between an unlocked and locked position by rotation through less than a 180 degree rotation relative to the plate. In other arrangements, the angle of rotation needed to move the cap from an unlocked to a locked position is in the range of about 15 to about 90 degrees, preferably in the range of about 15 to about 60 degrees, and more preferably in the range of about 35 to about 65 degrees.

While the above figures show a 2-level plate, one of ordinary skill in the art will recognize on reading the disclosure that the present invention would be useful for any number of levels.

While the invention has been particularly shown and described with reference to embodiments thereof, it will be understood by those skilled in the art that various other changes in the form and details may be made without departing from the spirit and scope of the invention.

We claim:

1. A bone plate assembly, comprising:
   a bone plate having at least one through hole at least one recess portion adjacent to the through hole, and a protrusion positioned in the at least one recess portion;
   at least one screw having a head portion sized to be retained in one of the through holes;
   a cap member including a body portion and at least one tab member, the body portion being configured to extend into the through hole and the tab member configured to extend into the recess portion, the cap member being rotatable to flex the tab member across the protrusion from an unlocked position to a locked positioned,
   wherein the recess portion includes a first portion and a second portion, the first portion being open to an anterior surface of the plate and to the through hole, and the second portion being open only to the through hole.

2. The bone plate assembly of claim 1, wherein the cap member includes at least two tab members, each tab member extending radially outward from the body portion.

3. The bone plate assembly of claim 1, wherein the plate includes an anterior surface and a posterior surface, the through hole extending from the anterior surface to the posterior surface, and the recess portion is generally parallel with that portion of the anterior surface adjacent to the through hole.

4. The bone plate assembly of claim 1, wherein the plate includes an anterior surface and a posterior surface, the through hole extending from the anterior surface to the posterior surface, and the recess portion lies between the anterior surface and the posterior surface.

5. The bone plate assembly of claim 1, wherein the protrusion is positioned between the first and second portions.

6. The bone plate assembly of claim 5, wherein rotating the tab member past the protrusion includes an increase and decrease in resistance that is adapted to provide a tactile feedback that the tab member has moved past the protrusion.

7. The bone plate assembly of claim 5, wherein rotating the tab member past the protrusion provides audible indicia indicating that the tab member has moved past the protrusion.

8. The bone plate assembly of claim 1, wherein the tab member includes a leading surface, the leading surface having a tapered portion, the leading surface being oriented facing the direction of movement from the unlocked position to the locked position.

9. A bone plate assembly, comprising:
   a bone plate having at least one through hole at least one recess portion adjacent to the through hole, and a protrusion positioned in the at least one recess portion;
   at least one screw having a head portion sized to be retained in one of the through holes;
   a cap member including a body portion and at least one tab member, the body portion being configured to extend into the through hole and the tab member configured to extend into the recess portion, the cap member being rotatable to flex the tab member across the protrusion from an unlocked position to a locked positioned, wherein the cap member includes a top surface and a bottom surface, the top surface including at least one recess sized to receive a portion of an installation instrument, and the bottom surface including a recess configured to receive a portion of the head portion of the screw.

10. An implantable device for affixing to adjacent vertebrae, comprising:
    a plate member including:
       an anterior surface and a posterior surface;
       a plurality of holes extending from the anterior surface to the posterior surface, each hole including an entrance portion and an exit portion, the exit portion including a transverse dimension;
       at least one locking recess open to and extending radially outward from one of the holes, the locking recess having a first portion being accessible from the anterior surface and in communication with the one of the holes and a second portion not being accessible from the anterior surface and in communication with the one of the holes;
       a locking protrusion residing in the locking recess;
    a screw including:
       a shank portion having a plurality of screw threads, the shank portion sized to extend through the exit portion of the hole; and
       a head portion having a maximum transverse dimension that is greater than the transverse dimension of the exit portion of the through hole; and
    a cap member including a body portion and at least one tab member, the body portion being sized to fit within the hole spaced from the head portion, and the tab member being insertable into the locking recess through the first portion and rotatable past the locking protrusion from an unlocked position to a locked position to secure the cap member to the plate member and retain the screw head in the hole.

11. The implantable device of claim 10, wherein the tab member is movable in the locking recess from an unlocked position to a locked position by rotation of the body portion in the hole.

12. A method of assembling a bone plate assembly, the bone plate assembly including a plate having at least one through hole and at least one locking recess having a first portion in communication with both an anterior portion of the plate and the at least one through hole and a second portion in communication with only the at least one through hole with a locking protrusion in the locking recess to resist movement of the tab member from a locked position to an unlocked position, a screw having a screw head, and at least one cap member having a body portion and a tab member, the method including:
    inserting the screw head into the through hole;
    inserting the body portion of the cap member into the through hole and the tab member into the first portion of the locking recess, the body portion covering at least a portion of the screw head to retain the screw head in the through hole; and
    rotating the cap member to flex the tab member past the locking protrusion from the unlocked position to the locked position in the locking recess, wherein the tab member resides in the second portion of the locking recess in the locked position.

13. The method of claim 12, wherein rotating the cap member includes rotation of less than 60 degrees.

14. The method of claim 12, wherein rotating the cap member increases the torsional resistance to rotation.

15. The method of claim 12, including inserting an instrument through the cap member to engage the screw head.

* * * * *